(12) United States Patent  
Okamoto et al.

(10) Patent No.: US 7,635,780 B2  
(45) Date of Patent: Dec. 22, 2009

(54) METHOD FOR PRODUCING FLUORINATED 1,3-DIOXOLANE COMPOUNDS, FLUORINATED 1, 3-DIOXOLANE COMPOUNDS, FLUORINATED POLYMERS OF THE FLUORINATED 1,3-DIOXOLANE COMPOUNDS AND OPTICAL OR ELECTRICAL MATERIALS USING THE POLYMERS

(75) Inventors: Yoshiyuki Okamoto, Fort Lee, NJ (US); Yasuhiro Koike, Yokohama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 522 days.

(21) Appl. No.: 10/570,210

(22) PCT Filed: Aug. 30, 2004

(86) PCT No.: PCT/JP2004/012866

§ 371 (c)(1),  
(2), (4) Date: Oct. 23, 2006

(87) PCT Pub. No.: WO2005/021526

PCT Pub. Date: Mar. 10, 2005

(65) Prior Publication Data

US 2007/0043187 A1     Feb. 22, 2007

Related U.S. Application Data

(60) Provisional application No. 60/498,689, filed on Aug. 29, 2003.

(30) Foreign Application Priority Data

Jun. 15, 2004     (JP) ............................. 2004-177125

(51) Int. Cl.  
*C07D 317/16*     (2006.01)  
*C07D 317/42*     (2006.01)

(52) U.S. Cl. .................................................. 549/455

(58) Field of Classification Search ................. 549/455  
See application file for complete search history.

(56) References Cited

U.S. PATENT DOCUMENTS

| | | | |
|---|---|---|---|
| 3,308,107 A | 3/1967 | Selman et al. | ............. 260/87.5 |
| 3,450,716 A | 6/1969 | Selman et al. | ............ 260/340.2 |
| 3,978,030 A | 8/1976 | Resnick | ....................... 526/247 |
| 4,429,143 A | 1/1984 | Anderson et al. | ........... 549/450 |
| 4,496,750 A | 1/1985 | Anderson et al. | ........... 549/455 |

FOREIGN PATENT DOCUMENTS

| | | |
|---|---|---|
| CA | 2464643 A1 | 5/2003 |
| JP | 5-213929 | 8/1993 |
| JP | 5-339255 | 12/1993 |
| JP | 10-031119 | 2/1998 |
| JP | 2002-71972 | 3/2002 |

OTHER PUBLICATIONS

"Synthesis of Some Derivatives of Perfluoro-4-Oxo-1,3-Dioxolane", Yuminov et al., A.N. Nesmeyanov Institute of Heteroorganic Compounds, Academy of Sciences of the USSR, Moscow, 1988, pp. 392-395.

(Continued)

*Primary Examiner*—Bernard Dentz  
(74) *Attorney, Agent, or Firm*—Marshall, Gerstein & Borun LLP (57) ABSTRACT

A production method of fluorinated compounds, for producing a compound represented by formula (3) in a fluorine-based solution in a flow of fluorine gas after reaction of at least one type of compounds represented by formula (1) and at least one type of compounds represented by formula (2). Similarly, fluorinated compounds represented by formula (4) prepared by the fluorination of compounds obtained by the reaction of formula (1) and formula (2)'. The fluorinated polymers obtained by the polymerizations of formula (3) and (4) compounds are useful as an optical or electrical materials.

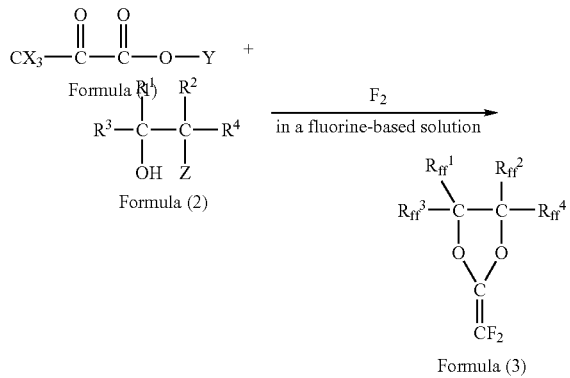

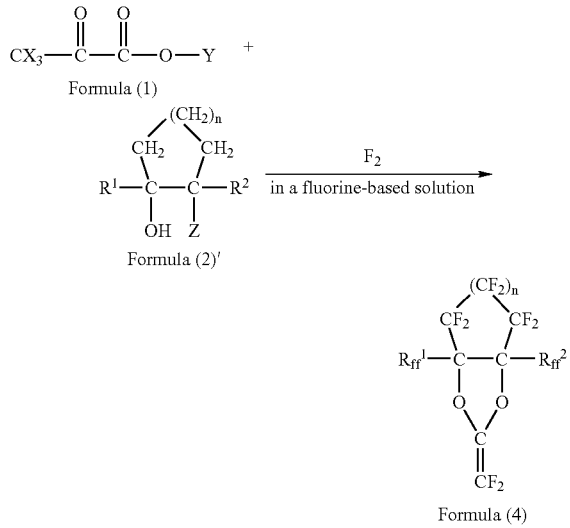

wherein $R^1, R^2, R^3, R^4, R_{ff}^1, R_{ff}^2, R_{ff}^3, R_{ff}^4, X, Y, Z$, and n are defined in the specification respectively.

3 Claims, 3 Drawing Sheets

OTHER PUBLICATIONS

"Nucleophilic Reactions of Perfluoro-4-Methyl-1,3-Dioxolanes", Yuminov et al., A.N. Nesmeyanov Institute of Heteroorganic Compounds, Academy of Sciences of the USSR, Moscow, 1989, pp. 938-942.

"A New Synthetic Procedure for the Preparation and Manufacture of Perfluoropolyethers", Lagow et al., 1992, pp. 97-126.

"Synthesis and Characterization of Poly(Perfluoro-2-Methylene-1,3-Dioxolanes)", Liu et al., Polymer Preprints 45(2), 2004, pp. 663-664.

International Search Report in PCT/JP2004/012866 dated May 3, 2005.

Written Opinion in PCT/JP2004/012866 dated May 3, 2005.

METHOD FOR PRODUCING FLUORINATED 1,3-DIOXOLANE COMPOUNDS, FLUORINATED 1,3-DIOXOLANE COMPOUNDS, FLUORINATED POLYMERS OF THE FLUORINATED 1,3-DIOXOLANE COMPOUNDS AND OPTICAL OR ELECTRICAL MATERIALS USING THE POLYMERS

BACKGROUND OF THE INVENTION

1. Technical Field

The present invention relates to a method for fluorinated compounds, fluorinated compounds produced by the method, fluorinated polymers obtained from the fluorinated compounds, and optical or electrical materials using the fluorinated polymers.

2. Related Art

Fluorinated polymers are useful materials that are used in various applications, for example, plastic optical fibers and photoresist materials, or surface modifiers. However, the synthetic processes of fluorinated polymers are complicated and costly.

A fluorinated polymer is obtained by polymerization of a fluorinated compound having a polymeric unsaturated group. As an example of fluorinated polymers, 1,3-dioxolane derivatives and the like are disclosed in U.S. Pat. No. 3,308,107, U.S. Pat. No. 3,450,716; Izvestiya A Kademii Nank SSSR, Seriya Khimicheskaya. pp. 392-395, February 1988 by V. S. Yuminov et al. and pp/938-, April 1989 by V. S. Yuminov et al; and the like.

However, 1,3-dioxolane derivatives that have been conventionally known are limited to the structures of a compound represented by the following formula (A) disclosed in U.S. Pat. No. 3,978,030, a compound represented by the following formula (B) disclosed in JP-A No. 5-339255, and the like. In these compounds, only a specific substitutional group can be located at a specified site on a five-membered ring of dioxolane.

Formula (A)

Formula (B)

In Formula (B), $R_f^{1'}$ and $R_f^{2'}$ each independently represent a polyfluoroalkyl group having 1 to 7 carbon atoms.

Such structural limitation results from the synthetic processes employed to form the polymers. For example, in a conventional method for synthesis of the compound represented by the above formula (A), only one fluorine-containing group may be located on a 1,3-dioxolane ring, and the fluorine-containing group that can be introduced is limited to a trifluoroalkyl group. In a conventional method for synthesis of the compound represented by the above formula (B), one polyfluoroalkyl group that can be introduced into a 1,3-dioxolane ring is located at each site of 4- and 5-membered rings, that is, the number of polyfluoroalkyl group is inevitably limited to two in total. Further, a material used for synthesizing the fluorinated compound represented by formula (B) is a compound represented by the following formula (C), and it is difficult to synthesize such compound.

Formula (C)

SUMMARY OF THE INVENTION

The present inventors have developed the following synthetic methods, therefrom have derived useful and novel fluorinated compounds, and optical or electrical materials using the polymers. The present invention will be described below.

A first aspect of the present invention is a method for producing a fluorinated compound represented by the following formula (3), the method comprising a step of fluorinating, in a fluorine-based solution under a fluorine gas atmosphere, a compound obtained by reacting at least one of kind of compound represented by the following formula (1) and at least one kind of compound represented by the follwing formula (2):

Formula (1)

Formula (2)

wherein in formula (1), X represents a hydrogen atom or a fluorine atom, and Y represents an alkyl group having 1 to 7 carbon atoms or a polyfluoroalkyl group having 1 to 7 carbon atoms; and in formula (2), Z represents a hydroxyl group, a chlorine atom, or a bromine atom, and $R^1$ to $R^4$ each independently represent a hydrogen atom, an alkyl group having 1 to 7 carbon atoms or a polyfluoroalkyl group having 1 to 7 carbon atoms.

Formula (3)

Wherein, in formula (3), $R_{ff}^1$ to $R_{ff}^4$ each independently represent a fluorine atom or a perfluoroalkyl group having 1 to 7 carbon atoms.

A second aspect of the present invention is the method for producing a fluorinated compounds according to the first aspect, wherein the fluorine gas atmosphere is a mixed atmosphere of nitrogen gas and fluorine gas, and a proportion of the nitrogen gas with respect to the fluorine gas is in a range from 2 to 4.

A third aspect of the present invention is the method for producing a fluorinated compounds according to the first aspect, wherein, in the step of fluorinating, a reaction temperature is kept in a range of 0 to 5° C., and stirring is carried out A fourth aspect of the present invention is a fluorinated compound represented by the following formula (4):

Formula (4)

wherein, in formula (4), $R_{ff}^1$ and $R_{ff}^2$ each independently represent a fluorine atom or a perfluoroalkyl group having 1 to 7 carbon atoms, and n represents an integer from 1 to 4.

A fifth aspect of the present invention is a fluorinated polymer obtained by polymerization of the fluorinated compound according to the fourth aspect.

A sixth aspect of the present invention is an optical or electrical material comprising the fluorinated polymer according to the fifth aspect.

A seventh aspect of the present invention is an optical or electrical material according to the sixth aspect, wherein the optical material is an optical wave guide, an optical lens, a prisms, a photo mask, or an optical fiber.

A eighth aspect of the present invention is a compound represented by the following formula (5):

Formula (5)

wherein, in formula (5) X represents a hydrogen atom or a fluorine atom, Y represents a hydrogen atom, an alkyl group having 1 to 7 carbon atoms, or a polyfluoroalkyl group having 1 to 7 carbon atoms, and $R^1$ to $R^4$ each independently represent a hydrogen atom, an alkyl group having 1 to 7 carbon atoms, or a polyfluoroalkyl group having 1 to 7 carbon atoms.

A ninth aspect of the present invention is a compound represented by the following formula (6):

wherein, in formula (6), X represents a hydrogen atom or a fluorine atom, Y represents a hydrogen atom, an alkyl group having 1 to 7 carbon atoms, or a polyfluoroalkyl group having 1 to 7 carbon atoms, $R^3$ or $R^4$ each independently represent a hydrogen atom, an alkyl group having 1 to 7 carbon atoms, or a polyfluoroalkyl group having 1 to 7 carbon atoms, and n represents an integer from 1 to 4.

DETAILED DESCRIPTION OF THE INVENTION

1. Method for Producing Fluorinated Compounds

A description will be given of a method for producing fluorinated compounds, that are 1,3-dioxolane derivatives, according to the present invention.

In the production method of the present invention, a fluorinated compound that uses 1,3-dioxolane derivatives, represented by the following formula (3), is produced using the following formulae (1) and (2) in a fluorine-based solution in a flow of fluorine gas.

Formula (1)

Formula (2)

Formula (3)

In Formula (1), X represents a hydrogen atom or a fluorine atom. From the viewpoint of ready availability, X is preferably a hydrogen atom. Y represents an alkyl group having 1 to 7 carbon atoms, preferably 1 to 3 carbon atoms, or a poly- fluoroalkyl group having 1 to 7 carbon atoms, preferably 1 to 3 carbon atoms, more preferably a perfluoroalkyl group having 1 to 3 carbon atoms. Specially preferably, Y represents an alkyl group having 1 to 3 carbon atoms In Formula (2), Z represents a hydroxyl group, chlorine atom, or bromine atom.

In Formula (2), $R^1$ to $R^4$ each independently represent a hydrogen atom, an alkyl group having 1 to 7 carbon atoms, or an polyfluoroalkyl group having 1 to 7 carbon atoms. After the compound represented by Formula (1) and the compound represented by Formula (2) are made to react with each other, hydrogen atoms that form a product are all fluorinated. Therefore $R^1$ to $R^4$ may be hydrogen atom, alkyl group, or polyfluoroalkyl group. More preferably, $R^1$ to $R^4$ each independently represent a hydrogen atom, or an alkyl group having 1 to 7 carbon atom because of cost-effective. Specifically preferably, $R^1$ to $R^4$ each independently represent a hydrogen atom, or an alkyl group having 1 to 3 carbon atom. $R^1$ and $R^2$ may be bonded to each other to form a ring.

In Formula (3), $R_{ff}^1$ to $R_{ff}^4$ each independently represent a fluorine atom, or a perfluoroalkyl group having 1 to 7 carbon atoms. Preferably, $R_{ff}^1$ to $R_{ff}^4$ each independently represent a fluorine atom, or a perfluoroalkyl group having 1 to 3 carbon atoms. $R_{ff}^1$ and $R_{ff}^4$ may be bonded to each other to form a ring.

Reaction schemes of these compounds are exemplified below, but the present invention is not limited to the same.

The production process of the present invention is broadly divided into, preferably, at least four steps as below.

(1) a step in which the compound represented by the above formula (1) and the compound represented by the above formula (2) are made to undergo dehydration or dehydro halogenation reaction;
(2) a step in which the above compounds are fluorinated in a fluorine-based solution;
(3) a step in which a carboxylate salt is produced by a base; and
(4) a step of heating in order to decarboxylate the obtained carboxylate salt.

These four steps (1) to (4) will be described below in detail.

Step (1):

It is preferable that the compound represented by Formula (1) and the compound represented by Formula (2) are made to react with each other at an equimolar ratio. The compounds represented by Formula (1) may be used either singly or in combination of two or more. Further, the compounds represented by Formula (2) may be used either singly or in combination of two or more.

Moreover, since the above is an exothermic reaction, these compounds are preferably made to react with each other while being cooled. Other reaction conditions are not particularly limited, and prior to the subsequent step (2), a purification process such as distillation is also preferably added.

Step (2):

In this step, hydrogen atoms of the compound prepared by the step (1) are all substituted with fluorine atoms. To that end, preferably, the hydrogen atoms are directly fluorinated in a fluorine-based solution. As for such direct fluorination, refer to Synthetic Fluorine Chemistry, Eds by G. A. Olah, R. D. Chambers, and G. K. S. Prakash, J. Wiley and Sons. Inc. New York (1992), by R. J. Lagow, T. R. Bierschenk, T. J. Juhlke and H. kawa, Chaper 5: Polyether Synthetic Method.

The fluorine-based solution is not particularly limited. For example, 1,1,2-trichlorotrifluoroethane, polyfluorobenzene, and the like are preferable. Specific examples thereof include Fluorinert FC-75, FC-77, FC-88 (produced by 3M Corporation), and the like. The ratio of fluorine-based solution to the compound prepared by the step (1) is 2-10 times (mass ratio), more preferably, the ratio is 3-4 times.

The fluorination is carried with fluorine gas diluted with nitrogen gas. The ratio of nitrogen gas to fluorine gas is preferably 2-6 times (volume ratio), more preferably, the ratio is 2-4 times larger than fluorine gas.

The compound obtained through the step (1) is dissolved in the fluorine-based solvent (the weight ratio of the compound to the solution is 0.40-0.50). The solution is added slowly into the fluorine-based solution under $F_2/N_2$ stream. The addition rate is preferably 0.3 ml/min. to 20 ml/min., more preferably 0.5 ml/min. to 10 ml/min.

The reaction of the step (2) is carried out by controlling temperature. The reaction temperature should be under 5° C., preferably at between 0° C. and 5° C. During step (2), the solution is preferably well stirred.

Step (3):

A carboxylate salt is produced from the fluorine compound obtained by step (2) by a base. As the base, potassium hydroxide, sodium hydroxide, cesium hydroxide, and the like are preferable. Potassium hydroxide is more preferable.

Step (4):

The obtained carboxylate salt is heated and decarboxylated. The heating temperature is preferably in the range of 250° C. to 320° C., and more preferably in the range of 270° C. to 290° C.

In the production method of the present invention, other steps in addition to the above steps (1) to (4) can be added.

2. Method for Producing Fluorinated Polymers

The above fluorinated compound undergoes radical polymerization in accordance with an ordinary method, thereby allowing production of a fluorinated polymer. A peroxide is preferably used as a radical catalyst, but in order that a fluorine atom of the fluorine compound may not be substituted with a hydrogen atom, a perfluoroperoxide is used.

3. Fluorinated Compound

In the production method of the present invention, a hydrogen atom can be substituted with a perfluoro group or a fluorine atom at an arbitrary site on a 1,3-dioxolane ring, and perfluoro-2-methylene-1,3-dioxolane represented by the following formula (3) can be obtained.

Formula (3)

In Formula (3), $R_{ff}^1$ to $R_{ff}^4$ each independently represent a fluorine atom, or a perfluoroalkyl group having 1 to 7 carbon atoms. Preferably, $R_{ff}^1$ to $R_{ff}^4$ each independently represent a fluorine atom, or a perfluoroalkyl group having 1 to 3 carbon atoms.

The compound represented by Formula (3) can be easily polymerized using a peroxide. Further, this compound has a five-membered ring and is a stable material. In the case of a six-membered ring, ring-opening is liable to occur at the time of polymerization, and therefore, a resulting polymer becomes a mixture. In this case, physical properties such as heat resistance are liable to deteriorate.

Further, a compound represented by the following formulae (4) is a novel compound.

Formula (4)

$R_{ff}^1$ and $R_{ff}^2$ each independently represent a fluorine atom, or a perfluoroalkyl group having 1 to 7 carbon atoms, and n represents an integer of 1 to 4, preferably, an integer of 1 to 2.

4. Method for Producing Fluorinated Polymers

The above fluorinated compound undergoes radical polymerization in accordance with an ordinary method, thereby allowing production of a fluorinated polymer. A peroxide is preferably used as a radical catalyst, but in order that a fluorine atom of the fluorine compound may not be substituted with a hydrogen atom, a perfluoroperoxide is used.

5. Application of Fluorinated Polymer

A polymer obtained by polymerization of the compound represented by Formula (4) can be suitably used for optical or electrical materials. This polymer has a high glass transition temperature and it is amorphous material. Therefore, such polymer can be suitably used for plastic optical fibers, light wave guides, optical lenses, prisms, photo masks, and the like, more suitably used for plastic optical fibers, light wave guides material, optical lenses.

EXAMPLE 1

Synthesis of perfluoro-4-methyl-2-methylene-1,3-dioxolane

Preparation of 2-carbomethyl-2-trifluoromethyl-4-methyl-1,3-dioxolane

A 3L 3-necked flask equipped with a water-cooled condenser, a thermometer, a magnetic stirrer and a pressure-equalizing dropping funnel were made usable. The flask was charged with 139.4 g (1.4 mol) of a mixture of 2-chloro-1-propanol and 1-chloro-2-propanol. The flask was cooled to 0° C. and methyl trifluoropyruvate was slowly added thereto. After addition, the reaction mixture was stirred for additional 2 hours. Then 100 ml of DMSO and 194 g of potassium carbonate were further added during one hour. Stirring was continued for another 8 hours, thereby obtaining a reaction mixture. The reaction mixture obtained was poured into 1 L of water. Dichloromethylene extracts were combined with the organic phase. Subsequently, the reaction mixture was dried with magnesium sulfate. After removing the solvent, 245.5 g of crude product was obtained. The crude product was fractionally distilled at reduced pressure (12 Torr), and 230.9 g of pure product of 2-carbomethyl-2-trifluoromethyl-4-methyl-1,3-dioxolane was obtained. The boiling point of the pure product was 77 to 78° C., and the yield was 77%.

HNMR (ppm): 4.2 to 4.6, 3.8 to 3.6 ($CHCH_2$, Multiplet, 3H), 3.85 to 3.88 ($COOCH_3$, multiplet, 3H), 1.36 to 1.43 ($CCH_3$, multiplet, 3H);

$^{19}$FNMR (ppm): −81.3 (CF3, s, 3F).

Fluorination of 2-carbomethyl-2-trifluoromethyl-4-methyl-1,3-dioxolane

A 10 L stirring-reactor vessel was loaded with 4 liters of 1,1,2-trichlorotrifluoroethane. The nitrogen flow was set at 1340 cc/min and the fluorine flow was set at 580 cc/min, thereby making the interior of the stirring-reactor vessel under a nitrogen/fluorine atmosphere. After 5 minutes, 290 g of the prepared 2-carbomethyl-2-trifluoromethyl-4-methyl-1,3-dioxolane was dissolved to 750 ml of 1,1,2-trichlorotrifluoroethane solution, and then this solution was added into the reactor at a rate of 0.5 ml/min. The reactor vessel was cooled to 0° C. After all the dioxolane was added over 24 hours, the fluorine flow was stopped. After purging with nitrogen gas, an aqueous KOH solution was added to the reactor until it turned to slight alkali.

After removing volatile materials under reduced pressure. The residue was further dried under reduced pressure at 70° C. for 48 hours, thereby obtaining a solid reaction product. The solid reaction product was dissolved in 500 ml of water and excess of hydrochloric acid was added to obtain two phases, that is, an organic phase and a water phase. The organic layer was separated and distilled under reduced pressure. As a result, perfluoro-2,4-dimethyl-1,3-dioxolane-2-carboxylic acid was produced. The boiling point of the main distillate was 103 to 106° C./100 mmHg. The overall fluorination yield was 85%.

Synthesis of perfluoro-4-methyl-2-methylene-1,3-dioxolane

Perfluoro-2,4-dimethyl-2-potassium carboxylate-1,3-dioxolane was obtained by neutralization of the above distillate with an aqueous KOH solution. The potassium salt was dried at 70° C. under vacuum for one day. The salt was decomposed with a stream of nitrogen or argon atmosphere at 250 to 280° C. to yield the product which was collected in a trap cooled to −78° C., thereby obtaining perfluoro-4-methyl-2-methylene-1,3-dioxolane (yield: 82%). The product had the boiling point of 45° C./760 mmHg, and was identified using $^{19}$FNMR and GC-MS as below.

$^{19}$FNMR: −84 ppm (3F, $CF_3$), −129 ppm (2F, $=CF_2$);

GC-MS: m/e244 (Molecular ion) 225, 197, 169, 150, 131, 100, 75, 50.

Synthetic schemes according to Example 1 are schematically shown below.

EXAMPLE 2

Polymerization of perfluoro-4-methyl-2-methylene-1,3-dioxolane 100 g of perfluro-4-methyl-2-methylene-1,3-dioxolane and 1 g of perfluorobenzoyl peroxide were charged in a glass tube, which was then degassed and refilled with argon in two vacuum freeze-thaw cycles. The tube was sealed and heated at 50° C. for several hours. The content became solid. Further the tube was kept to be heated at 70° C. over night and 100 g of a transparent bar was obtained.

The transparent bar was dissolved in Fluorinert FC-75 (produced by 3M Corporation) and a thin film of polymer was obtained by casting the solution on a glass plate. The glass transition temperature of the polymer was 117° C. The polymer was completely amorphous. The transparent bar was purified by precipitation from the hexafluorobenzene solution by adding chloroform thereto. The glass transition temperature of the product was increased to 133° C.

Figure 1:
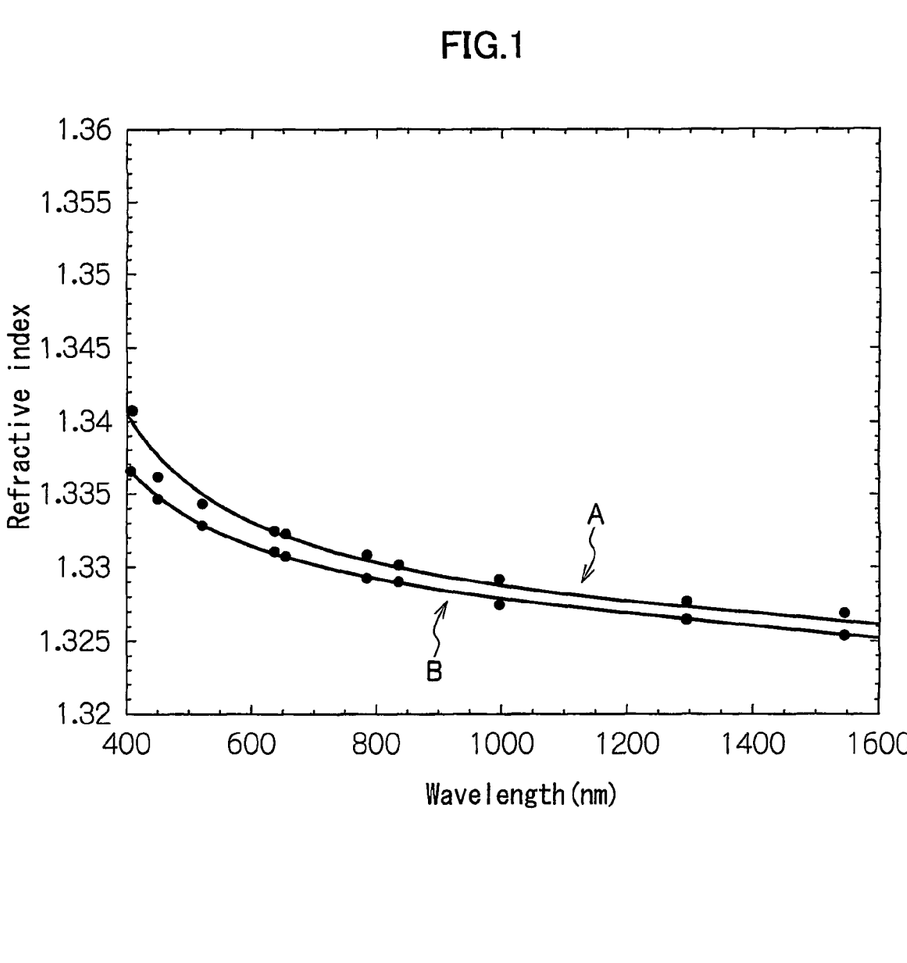
FIG. 1 is a graph showing refractive indexes of polymers synthesized by Examples 2 and 4.
Figure 2:
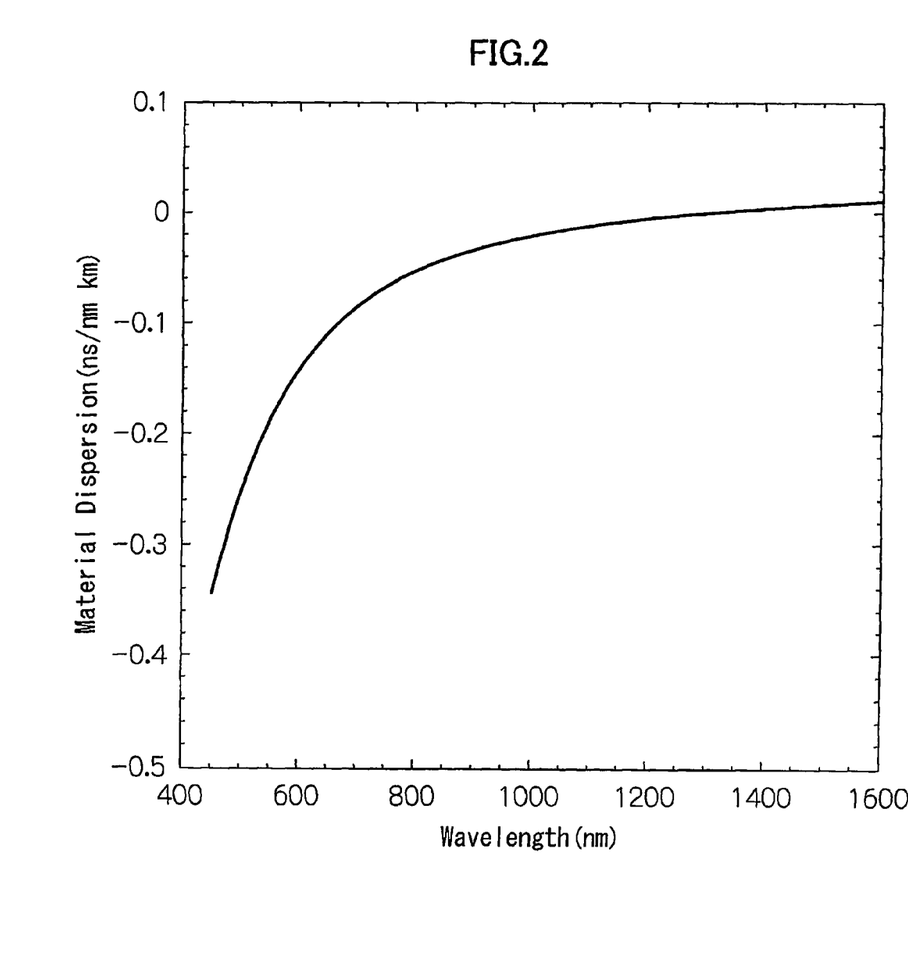
FIG. 2 is a graph showing the material dispersion of the polymer synthesized by Example 2.

The refractive indexes at various wavelengths were shown by the line of A in FIG. 1, and the material dispersion of the polymer was shown in FIG. 2. It can be seen from such refractive indexes that the obtained polymer is suitable for optical fibers, optical waveguides, and photo masks.

EXAMPLE 3

Synthesis of perfluoro-4,5-dimethyl-2-methylene-1,3-dioxolane

Synthesis of 2,4,5-trimethyl-2-carboxymethyl-1,3-dioxolane

A reaction mixture: 2.0 mol of 2,3-butanediol, 2.0 mol of methyl pyruvate, 10 g of a cation exchange resin (H form), and 1 L of absolute benzene were refluxed until no more water came to be produced in a flask fitted with a Dean-Stark trap, thereby obtaining 2,4,5-trimethyl-2-carboxymethyl-1,3-dioxolane. The yield was 75% and the boiling point of the product was 45° C./1.0 mmHg.

$^1$HNMR: 1.3 ppm (6H, —CH$_3$), 1.56 ppm (3H, —CH$_3$), 3.77 ppm (3H, OCH$_3$), 3.5 to 4.4 ppm (m, 2H, —OCH—).

Synthesis of perfluro-2,4,5-trimethyl-2-carboxylic acid-1,3-dioxolane

500 g of the obtained 2,4,5-trimethyl-2-carboxymethyl-1,3-dioxolane was fluorinated with fluorine gas diluted with nitrogen in Fluorinert FC-75 (trade name) as described in Example 1. After completion of the reaction, nitrogen gas was purged for 30 minutes. The obtained mixture was then treated with an aqueous KOH solution to form an organic phase and a slightly-alkaline water phase. The water of the water phase was removed under reduced pressure, and a solid material was thereby obtained. The solid material obtained was acidified with concentraded hydrochloric acid and distilled out, thereby obtaining perfluoro-2,4,5-trimethyl-2-carboxylic acid-1,3-dioxolane. The yield was 85%, and the boiling point was 61° C./2.5 mmHg.

Synthesis of perfluoro-4,5-dimethyl-2-methylene-1,3-dioxolane

Perfluoro-2,4,5-trimethyl-2-potassium carboxylate-1,3-dioxolane was obtained by neutralization of the above distillate with an aqueous KOH solution. The obtained potassium salt was dried at 70° C. under vacuum for one day. The salt was further decomposed with stream of nitrogen or argon at 250 to 280° C. to yield the product which was collected in a trap cooled to −78° C. As a result, perfluoro-4,5-dimethyl-2-methylene-1,3-dioxolane was obtained (yield: 78%). The boiling point of the product was 60° C. The product was identified using $^{19}$FNMR and GC-MS.

$^{19}$FNMR: −80 ppm (6F, —CF$_3$), −129 ppm (2F, =CF$_2$); GC-MS: m/e294 (Molecular ion).

Synthetic schemes according to Example 2 are schematically shown below.

EXAMPLE 4

Polymerization of perfluoro-4,5-dimethyl-2-methylene-1,3-dioxolane 10 g of the perfluoro-4,5-dimethyl-2-methylene-1,3-dioxolane obtained by Example 3 and 80 mg of perfluorobenzoylperoxide were charged in a glass tube, which was then degassed and refilled with argon in three vacuum freeze-thaw cycles. The tube was sealed and heated at 50° C. for one day. The content became solid and the tube was kept to be heated at 70° C. for 4 days. 10 g of a transparent bar was obtained.

The transparent bar was purified by dissolving a part thereof in a hexafluorobenzene solution and also by precipitation from a hexafluorobenzene solution with chloroform being added thereto. The yield was 98% or greater. Solution polymerization of the monomer was performed in Fluorinert FC-75 (trade name) using perfluorobenzoyl peroxide as an initiator.

Figure 3:
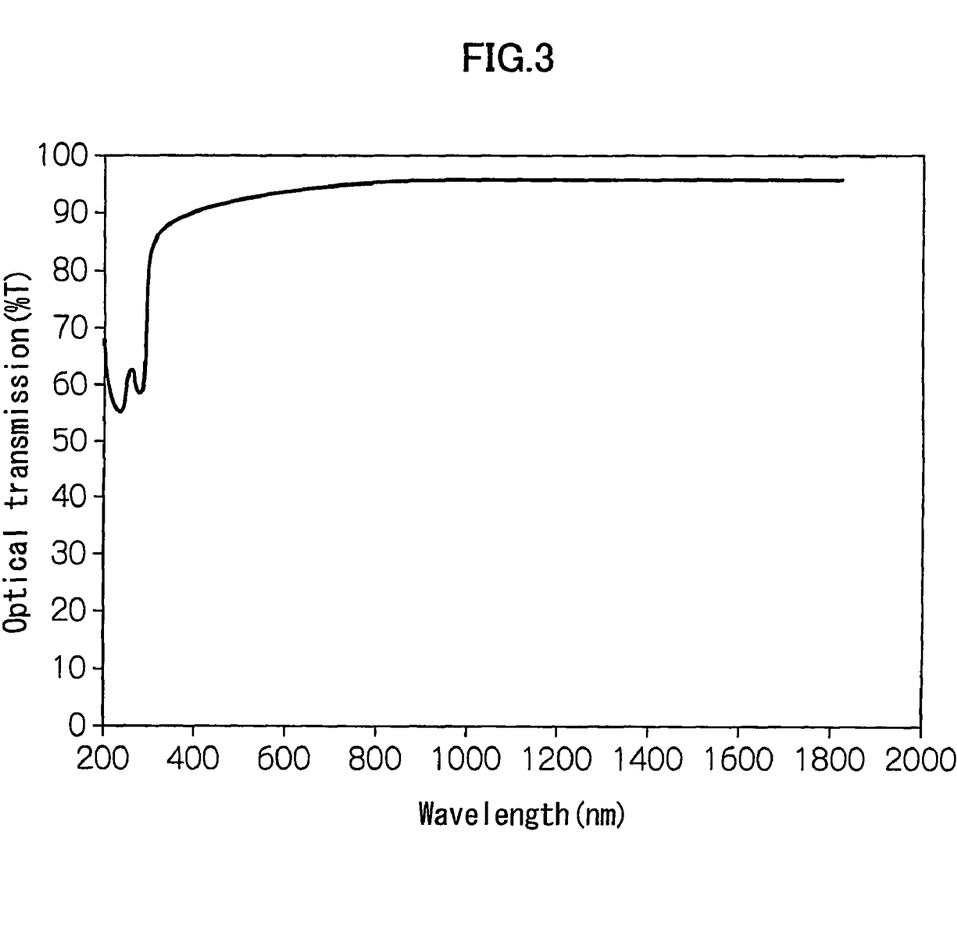
FIG. 3 is a graph showing the optical transmission of the polymer synthesized by Example 4.

$^{19}$FNMR of the obtained polymer was −80 ppm (6F, —CF$_3$), −100 to −120 ppm (2F, main chain) and −124 ppm (2F, —OCF). The refractive indexes of the obtained polymer are shown by the line B in FIG. 1, and the optical transmission thereof in the range of 200 to 2000 nm is shown in FIG. 3. It can be seen from such refractive indexes and optical transmission that the obtained polymer is suitable for optical fibers, optical wave guides, and photo masks.

EXAMPLE 5

Synthesis of perfluoro-4,5-cyclotetramethylene-2-methylene-1,3-dioxolane

Synthesis of 2-methyl-2-methoxycarboxyl-4,5-cyclotetramethylene-1,3-dioxolane:

A reaction mixture: 100 g (1 mol) of 1,2-cyclohexanediol, 204 g (2 mols) of methyl pyruvate, 1.5 L of absolute benzene, and 10 g of a cation exchange resin (H form) was refluxed until no more water came to be produced in a flask fitted with a Dean-Stark trap. The cation exchange resin was removed by filtration. The product was distilled at 65° C./5 mmHg, thereby obtaining 2-methyl-2-methoxycarboxyl-4,5-cyclotetramethylene-1,3-dioxolane. The yield was 50 to 60%.

Fluorination of 2-methyl-2-methoxycarboxyl-4,5-cyclotetramethylene-1,3-dioxolane The obtained 2-methyl-2-methoxycarboxyl-4,5-cyclotetramethylene-1,3-dioxolane was fluorinated in a fluorinated solvent, Fluorinert FC-75 (trade name) with F$_2$/N$_2$ as described in Example 1. After completion of the reaction, by removing the solvent and produced hydrogen fluoride, and then treating the fluorinated product with an aqueous KOH solution, perfluoro-2-methyl-2-potassium carboxylate-4,5-cyclotetramethylene-1,3-dioxolane was obtained. The obtained potassium salt was dried by heating at 60° C. under reduced pressure (yield: 75%) and the dried potassium salt was decomposed at 250° C. in the nitrogen gas atmosphere. The product; perfluoro-4,5-cyclotetramethylene-2-methylene-1,3-dioxolane was collected in a trap cooled to −78° C. and the yield thereof was 85%. The boiling point of the product was 60° C. The product was identified using $^{19}$FNMR and GC-MS.

$^{19}$FNMR: −137 ppm (2F, =CF$_2$), 126 to 134 ppm (8F, CF$_2$), −125 ppm (2F, OCF);

GC-MS: m/e360 (Molecular ion).

Synthetic schemes according to Example 5 are schematically shown below.

EXAMPLE 6

Polymerization of perfluoro-4,5-cyclotetramethylene-2-methylene-1,3-dioxolane 10 g of the perfluoro-4,5-cyclotetramethylene-2-methylene-1,3-dioxolane obtained by Example 5 and 80 mg of perfluorobenzoyl peroxide were charged in a glass tube, which was then degassed and refilled with argon in two vacuum freeze-thaw cycles. The tube was sealed and heated at 50° C. for 12 hours. The content of tube became solid and the tube was kept to be heated at 70° C. over night. 10 g of a transparent rod was obtained.

The resulting polymer was completely amorphous and transparent. The refractive indexes of the polymer were 1.3160 (632.8 nm) and 1.3100 (1544 nm), and the glass transition temperature thereof was about 160° C.

$^{19}$FNMR: −120 to −140 ppm (8F, CF$_2$), −100 to −118 ppm (2F, main chain), and 120 ppm (2F, —OCF). It can be seen from the viewpoint of a high glass transition temperature that the obtained polymer is less subject to heat deformation, and is suitable for electrical materials, optical fibers, optical wave guides, and the like.

EXAMPLE 7

Synthesis of perfluoro-4,5-cyclotrimethylene-2-methylene-1,3-dioxolane

Synthesis of 2-methyl-2-methoxycarboxyl-4,5-cyclotrimethylene-1,3-dioxolane

A reaction mixture: 102 g (1 mol) of 1,2-cyclopentanediol, 204 g (2 mols) of methyl pyruvate, 1.5 L of absolute benzene, and 10 g of a cation exchange resin (H form) was refluxed until no more than water came to be produced. After the cation exchange resin was removed by filtration, the product was distilled at 67° C./20 mmHg, thereby obtaining 2-methyl-2-methoxycarboxyl-4,5-cyclotrimethylene-1,3-dioxolane. The yield was 60 to 70%.

55

Fluorination of 2-methyl-2-methoxycarboxyl-4,5-cyclotrimethylene-1,3-dioxolane

The obtained 2-methyl-2-methoxycarboxyl-4,5-cyclotrimethylene-1,3-dioxolane was fluorinated in a fluorinated solvent, Fluorinert FC-75 (trade name) with F$_2$/N$_2$ as described in Example 1. The reaction product was treated with potassium hydroxide to thereby produce perfluoro-2-methyl-2-potassium carboxylate-4,5-cyclotrimethylene-1,3-dioxolane. The potassium salt obtained was dried by heating at 60° C. under reduced pressure. The yield was 82%. The dried potassium salt was decomposed at 260° C. in the flow of argon gas. The crude product was distilled at 85° C. to produce perfluoro-4,5-cyclotrimethylene-2-methylene-1,3-dioxolane (yield: 79%).

Synthetic schemes according to Example 7 are schematically shown below.

EXAMPLE 8

Polymerization of perfluoro-4,5-cyclotrimethylene-2-methylene-1,3-dioxolane 20 g of the perfluoro-4,5-cyclotrimethylene-2-methylene-1,3-dioxolane obtained by Example 5 and 150 mg of perfluorobenzoyl peroxide were charged in a glass tube. The polymerization was carried out as described in Example 2. A transparent amorphous polymer was obtained. The glass transition temperature of the polymer was found to be 150° C.

As described above, the polymers obtained are highly transparent and amorphous and also have a high glass transition temperature, and therefore, they are found as excellent materials that can be used for various applications of optical fibers, electrical materials, and the like.

The invention claimed is:

1. A method for producing a fluorinated compound represented by the following formula (3), the method comprising a step of fluorinating, in a fluorine-based solution under a fluorine gas atmosphere, a compound obtained by reacting at least one compound represented by the following formula (1) and at least one compound represented by the following formula (2):

Formula (1)

Formula (2)

wherein in formula (1), X represents a hydrogen atom or a fluorine atom, and Y represents an alkyl group having 1 to 7 carbon atoms or a polyfluoroalkyl group having 1 to 7 carbon atoms; and in formula (2), Z represents a hydroxyl group, a chlorine atom, or a bromine atom, and R$^1$ to R$^4$ each independently represent a hydrogen atom, an alkyl group having 1 to 7 carbon atoms, or a polyfluoroalkyl group having 1 to 7 carbon atoms Formula (3)

wherein, in formula (3), $R_{ff}^1$ to $R_{ff}^4$ each independently represent a fluorine atom or a perfluoroalkyl group having 1 to 7 carbon atoms.

2. The method for producing a fluorinated compound according to claim 1, wherein the fluorine gas atmosphere is a mixed atmosphere of nitrogen gas and fluorine gas, and the proportion of the nitrogen gas with respect to the fluorine gas is in a range from 2 to 4.

3. The method for producing a fluorinated compound according to claim 1, wherein, in the step of fluorinating, a reaction temperature is kept in a range of 0 to 5° C., and stirring is carried out.

\* \* \* \* \*